US012631615B2

(12) United States Patent
Kim et al.

(10) Patent No.: US 12,631,615 B2
(45) Date of Patent: May 19, 2026

(54) TRANSFORMER MALFUNCTION DIAGNOSIS DEVICE AND MALFUNCTION DIAGNOSIS METHOD USING SAME

(71) Applicant: SEOUL NATIONAL UNIVERSITY R&DB FOUNDATION, Seoul (KR)

(72) Inventors: Sun Uwe Kim, Seoul (KR); Byeng Dong Youn, Seoul (KR); Soo Ho Jo, Seoul (KR); Jong Min Park, Seoul (KR); Won Gon Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 397 days.

(21) Appl. No.: 18/260,090

(22) PCT Filed: Oct. 1, 2021

(86) PCT No.: PCT/KR2021/013531
§ 371 (c)(1),
(2) Date: Jun. 30, 2023

(87) PCT Pub. No.: WO2022/145642
PCT Pub. Date: Jul. 7, 2022

(65) Prior Publication Data
US 2024/0053323 A1 Feb. 15, 2024

(30) Foreign Application Priority Data

Dec. 30, 2020 (KR) ........................ 10-2020-0187981
Sep. 16, 2021 (KR) ........................ 10-2021-0124138

(51) Int. Cl.
*G01N 33/28* (2006.01)
*G06N 3/084* (2023.01)

(52) U.S. Cl.
CPC ......... *G01N 33/2841* (2013.01); *G06N 3/084* (2013.01)

(58) Field of Classification Search
CPC .... G01N 33/2841; G01N 33/28; G06N 3/084; G06N 3/0499; G06N 3/08; G06N 3/0895;
(Continued)

(56) References Cited

U.S. PATENT DOCUMENTS 8,751,421 B2 6/2014 Anderson et al.
9,176,107 B2 * 11/2015 Jeffrey ............... G01N 33/2841
(Continued)

FOREIGN PATENT DOCUMENTS

CN 106596900 A 4/2017
KR 10-2013-0074674 A 7/2013
(Continued)

OTHER PUBLICATIONS

Sunuwe Kim et al., "A Semi-Supervised Autoencoder With an Auxiliary Task (SAAT) for Power Transformer Fault Diagnosis Using Dissolved Gas Analysis," IEEE Access, 2020, pp. 178295-178310, vol. 8, DOI: 10.1109/ACCESS.2020.3027830.

*Primary Examiner* — Manuel A Rivera Vargas

(57) ABSTRACT

The present invention provides a transformer malfunction diagnostic device and a malfunction diagnosis method using same, wherein a rule-based learning method is combined with a deep-learning-based learning method based on artificial intelligence. The transformer malfunction diagnosis device according to an embodiment of the present invention comprises: a data scaling unit for scaling dissolved gas analysis data acquired from a transformer, a provisionally labeled data acquisition unit for converting unlabeled data, among the scaled dissolved gas analysis data, to provisionally labeled data and acquiring same; a prelearning unit for performing prelearning for the unlabeled data, among the scaled dissolved gas analysis data, and the provisionally labeled data; and a relearning unit for performing relearning
(Continued)

for a labeled data through the transformer of parameters optimized by performing the prelearning.

18 Claims, 6 Drawing Sheets

(58) Field of Classification Search
CPC ........ G06N 3/09; G06N 3/096; G06N 3/0985; H01F 27/12; H01F 27/40
See application file for complete search history.

(56) References Cited

U.S. PATENT DOCUMENTS

| | | | | |
|---|---|---|---|---|
| 2016/0327600 | A1* | 11/2016 | Pamulaparthy | .......... H02H 7/04 |
| 2019/0056446 | A1* | 2/2019 | Dukarm | ................. G01R 31/62 |
| 2019/0207388 | A1* | 7/2019 | Li | ........................... G06Q 10/06 |
| 2021/0048488 | A1* | 2/2021 | Das | ......................... G01R 31/62 |
| 2021/0270797 | A1* | 9/2021 | Cheim | ............... G01N 33/2841 |
| 2021/0397895 | A1* | 12/2021 | Sun | ........................ G06N 3/084 |
| 2022/0137612 | A1* | 5/2022 | He | ........................... G01J 5/00 700/292 |

FOREIGN PATENT DOCUMENTS

| | | |
|---|---|---|
| KR | 10-01731218 B1 | 4/2017 |
| KR | 10-1842831 B1 | 5/2018 |
| KR | 10-2019-0034963 A | 4/2019 |
| KR | 10-2007231 B1 | 10/2019 |
| KR | 10-2020-0014129 A | 2/2020 |
| KR | 10-2128460 B1 | 6/2020 |

* cited by examiner

FIG. 1

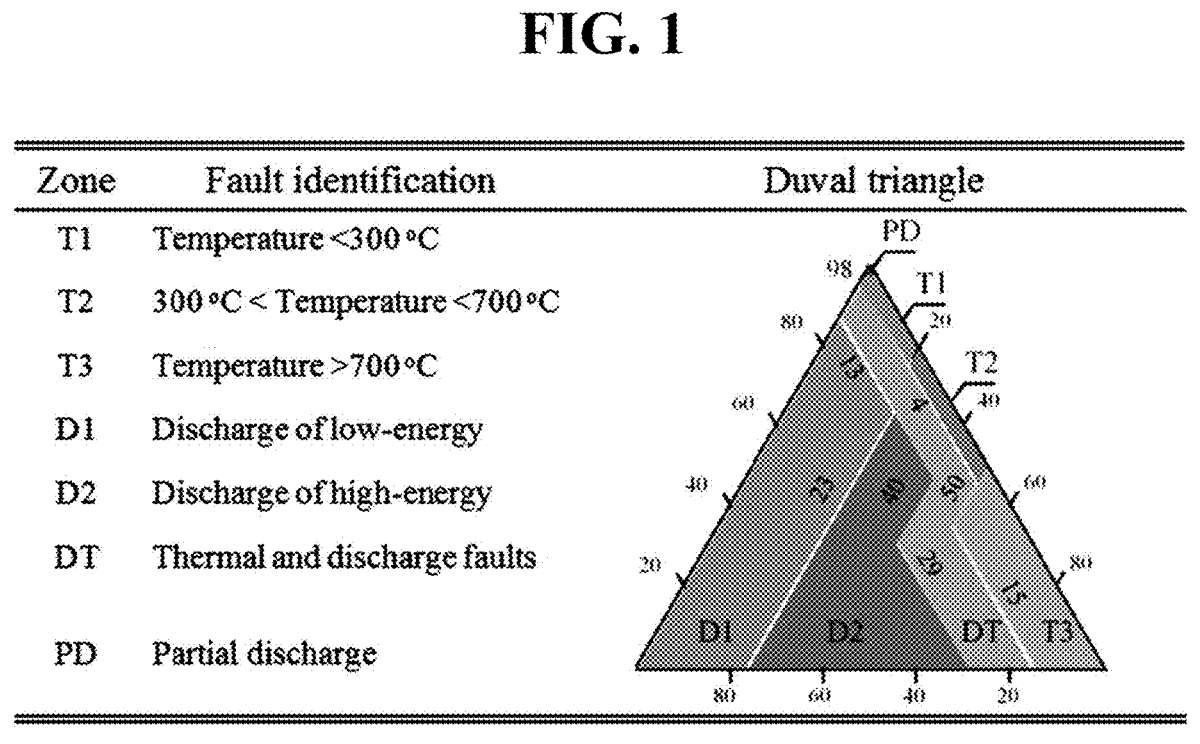

| Zone | Fault identification | Duval triangle |
|------|---------------------|----------------|
| T1 | Temperature <300 °C | |
| T2 | 300 °C < Temperature <700 °C | |
| T3 | Temperature >700 °C | |
| D1 | Discharge of low-energy | |
| D2 | Discharge of high-energy | |
| DT | Thermal and discharge faults | |
| PD | Partial discharge | |

FIG. 2

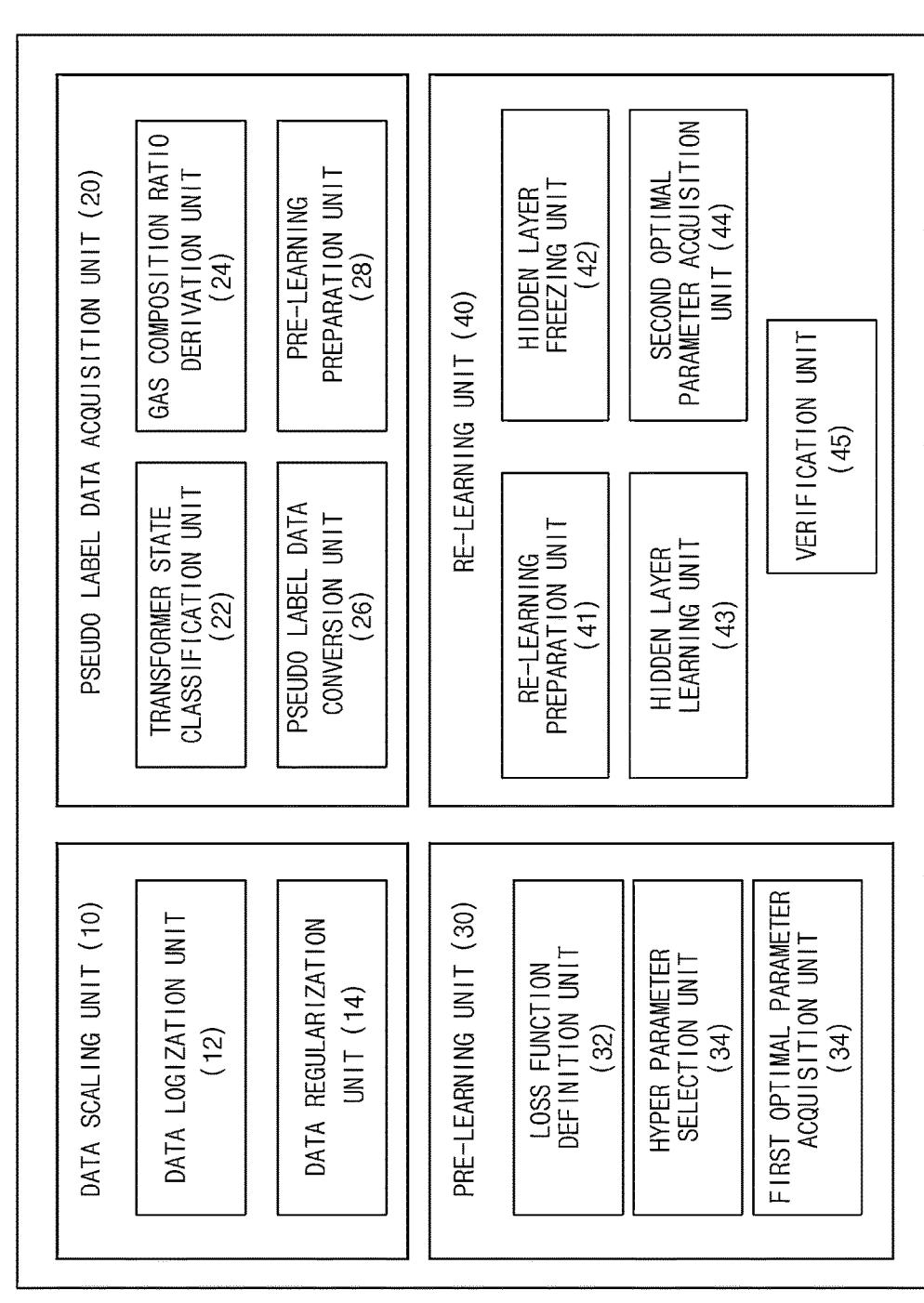

100

PSEUDO LABEL DATA ACQUISITION UNIT (20)

TRANSFORMER STATE CLASSIFICATION UNIT (22)

GAS COMPOSITION RATIO DERIVATION UNIT (24)

PSEUDO LABEL DATA CONVERSION UNIT (26)

PRE-LEARNING PREPARATION UNIT (28)

RE-LEARNING UNIT (40)

RE-LEARNING PREPARATION UNIT (41)

HIDDEN LAYER FREEZING UNIT (42)

HIDDEN LAYER LEARNING UNIT (43)

SECOND OPTIMAL PARAMETER ACQUISITION UNIT (44)

VERIFICATION UNIT (45)

DATA SCALING UNIT (10)

DATA LOGIZATION UNIT (12)

DATA REGULARIZATION UNIT (14)

PRE-LEARNING UNIT (30)

LOSS FUNCTION DEFINITION UNIT (32)

HYPER PARAMETER SELECTION UNIT (34)

FIRST OPTIMAL PARAMETER ACQUISITION UNIT (34)

$$X_S^{(m)} = [H_2, C_2H_2, \cdots, CH_4]$$

Spanning into Duval triangle

Unlabeled DGA sample

Pseudo-labeled: $(X_S^{\star}, \tilde{Y}_S)$

FIG. 6

EVALUATION OF THE FAULT DIAGNOSIS ACCURACY

| Learning approaches | Methods | Ratio (%) of labeled training data | | | | | Unlabeled |
|---|---|---|---|---|---|---|---|
| | | 5 | 10 | 30 | 60 | 80 | |
| Supervised learning | L-SVM | 50.0 | 54.5 | 63.6 | 68.2 | 68.2 | X |
| | R-SVM | 40.9 | 40.9 | 45.5 | 50.0 | 54.5 | |
| | KNN | 40.9 | 40.9 | 59.1 | 72.7 | 72.7 | |
| | 1-NN | 50.0 | 40.9 | 50.0 | 50.0 | 59.1 | |
| | DeA | 13.6 | 18.2 | 22.7 | 77.2 | 86.4 | |
| | DNN | 50.0 | 63.6 | 68.2 | 81.8 | 90.9 | |
| Semi-supervised learning | L-SVM | 40.9 | 45.5 | 63.6 | 63.6 | 59.1 | O |
| | R-SVM | 50.0 | 63.6 | 72.7 | 77.3 | 68.2 | |
| | KNN | 45.5 | 50.0 | 59.1 | 63.6 | 68.2 | |
| | 1-NN | 40.9 | 63.6 | 63.6 | 63.6 | 72.7 | |
| | DeA | 50.0 | 54.5 | 68.1 | 77.2 | 86.4 | |
| | DNN | 50.0 | 63.6 | 72.7 | 77.3 | 86.4 | |
| Rule-based knowledge learning | L-SVM | 45.5 | 45.5 | 45.5 | 50.0 | 50.0 | △ |
| | R-SVM | 63.6 | 72.7 | 77.3 | 81.8 | 81.8 | |
| | KNN | 54.5 | 54.5 | 59.1 | 63.6 | 63.6 | |
| | 1-NN | 59.1 | 63.6 | 63.6 | 77.3 | 72.7 | |
| | DeA | 63.6 | 68.2 | 77.3 | 81.8 | 81.8 | |
| | $DNN_{FT}^{Non}$ | 77.2 | 77.2 | 81.8 | 81.8 | 81.8 | |
| | $DNN_{PF}^{Non}$ | 77.3 | 81.8 | 86.4 | 86.4 | 90.9 | |
| | $DNN_{FT}^{Aux}$ | 81.8 | 81.8 | 81.8 | 86.4 | 86.4 | |
| | BDD | 86.4 | 90.9 | 95.4 | 95.4 | 95.4 | |

TRANSFORMER MALFUNCTION DIAGNOSIS DEVICE AND MALFUNCTION DIAGNOSIS METHOD USING SAME

TECHNICAL FIELD

The present invention relates to a transformer malfunction diagnosis device and a malfunction diagnosis method using the same, and particularly, to a transformer malfunction diagnosis device using dissolved gas analysis data and a malfunction diagnosis method using the same.

BACKGROUND ART

In general, an oil immersed transformer installed in substations or power companies is one of the power supply systems, and as the demand and capacity of power continues to increase, the oil immersed transformer is one of the very important components of the power supply system, and requires high reliability maintenance.

Electrical or mechanical performance of the oil immersed transformer deteriorates due to degradation during operating, which may cause abnormality, and when such a phenomenon is sensed in advance, an appropriate measure is not taken, which may cause a serious accident, and serious economic and social chaos may be caused in addition to power loss.

When an abnormal phenomenon such as insulation destruction and local overheating occurs inside the oil immersed transformer, heat generation should be accompanied, and insulating materials such as insulation oil, insulation paper, press board, etc., which contact such a heat generation source, are influenced by heat, so the insulating materials are dissolved by a chemical reaction, which generates gases. In this case, most gases are dissolved in the insulation oil, and when the insulation oil of the oil immersed transformer is collected, and the gas is extracted and analyzed, a defect which occurs inside the oil immersed transformer and a degree thereof may be diagnosed.

The diagnosis method of the oil immersed transformer using the dissolved gas analysis (DGA) requires very complex procedures and efforts, but widely used worldwide because of its high hit rate as internal defect diagnosis of the oil immersed transformer.

Recently, a deep-learning scheme is being studied to diagnose a malfunction mode of the oil immersed transformer using the dissolved gas analysis. Such a study ideally adds unsupervised learning with more data sets that can be learned to show more accurate performance than a conventional shallow learning scheme.

However, in the case of using the deep-learning scheme, a malfunction diagnosis method of the oil immersed transformer shows a slightly unreliable low diagnosis performance if there are only vast amount of unlabeled data and rare labeled data. In order to improve this problem, there is an effort to solve the unlabeled data by the unsupervised learning while using the deep learning scheme, but there are still many limitations and challenges, and to solve this problem, in a deep learning field, a focus has recently been on improving the accuracy of a deep learning model by using an existing scheme rather than creating a difficult and complex model in the deep learning field.

DISCLOSURE

Technical Problem

An object of the present invention is to provide a transformer malfunction diagnosis device which bridges a rule-based learning method and a deep learning based learning method based on artificial intelligence, and a malfunction diagnosis method using the same.

Technical Solution

According to an embodiment of the present invention, a transformer malfunction diagnosis device includes: a data scaling unit scaling dissolved gas analysis data acquired from the transformer; a pseudo label data acquisition unit converting unlabeled data among the scaled dissolved gas analysis data into pseudo label data, and acquiring the pseudo label data; a pre-learning unit performing pre-learning for the unlabeled data and the pseudo label data among the scaled dissolved gas analysis data; and a re-learning unit performing re-learning for labeled data through transfer of a parameter optimized by performing the pre-learning.

Preferably, the data scaling unit includes a data logization unit logizating the dissolved gas analysis data, and a data regularization unit regularizing the logizated dissolved gas analysis data.

Preferably, the pseudo label data acquisition unit includes a transformer state classification unit classifying a normal state and a malfunction state of the transformer by using the unlabeled data among the scaled dissolved gas analysis data, a gas composition ratio derivation unit selecting three combustible gases, and deriving gas composition ratios from concentrations of respective combustible gases, a pseudo label data conversion unit converting the unlabeled data among the scaled dissolved gas analysis data into the pseudo label data by applying the derived gas composition ratios to a Duval's triangle method, and a pre-learning preparation unit preparing for the unlabeled data and the pseudo label data among the scaled dissolved gas analysis data.

Preferably, the three combustible gases are $C_2H_2$, $C_2H_4$, and $CH_4$.

Preferably, the pre-learning unit includes a loss function definition unit defining a loss function $$L_{DNN}(\theta) = \alpha L_{su}(\hat{Y}_s, \hat{Y}_{end}) + (1 - \alpha)L_{un}(X_s^*, \hat{X}_{end}^*)$$

of a deep neural network, a hyper parameter selection unit selecting a hyper parameter $\alpha$ for adjusting a first term $L_{su}$ and a second term, $L_{un}$ in right terms of the loss function, and a first optimal parameter acquisition unit acquiring an optimal parameter by using a backpropagation method so as to optimize the loss function.

Preferably, in the loss function, $L_{su}$ represents a difference between pseudo label data $\hat{Y}_s$ acquired through a Duval's triangle method and pseudo label data $\hat{Y}_{end}$ estimated in a last layer among hidden layers of the deep neural network.

Preferably, in the loss function, $L_{un}$ represents a difference between unlabeled data $$X_s^*$$

among the scaled dissolved gas analysis data and dissolved gas analysis data $$\hat{X}_{end}^*$$

estimated in the last layer among the hidden layers of the deep neural network.

Preferably, the re-learning unit includes a re-learning preparation unit preparing for learning of the labeled data, a hidden layer freezing unit freezing some hidden layers of the deep neural network, a hidden layer learning unit performing learning only for the last hidden layer other than the freezing hidden layers, and a second optimal parameter acquisition unit acquiring the optimal parameter by using the backpropagation method so as to optimize the loss function.

Preferably, the hidden layer freezing unit freezes the remaining hidden layers other than the last hidden layer.

According to an embodiment of the present invention, a transformer malfunction diagnosis method includes: scaling dissolved gas analysis data acquired from the transformer; converting unlabeled data among the scaled dissolved gas analysis data into pseudo label data, and acquiring the pseudo label data; performing pre-learning for the unlabeled data and the pseudo label data among the scaled dissolved gas analysis data; and performing re-learning for labeled data through transfer of a parameter optimized by performing the pre-learning.

Preferably, the scaling of the dissolved gas analysis data includes logizating the dissolved gas analysis data, and regularizing the logizated dissolved gas analysis data.

Preferably, the converting of the unlabeled data among the scaled dissolved gas analysis data into pseudo label data, and acquiring of the pseudo label data includes classifying a normal state and a malfunction state of the transformer by using the unlabeled data among the scaled dissolved gas analysis data, selecting three combustible gases, and deriving gas composition ratios from concentrations of respective combustible gases, converting the unlabeled data among the scaled dissolved gas analysis data into the pseudo label data by applying the derived gas composition ratios to a Duval's triangle method, and preparing for the unlabeled data and the pseudo label data among the scaled dissolved gas analysis data.

Preferably, the three combustible gases are $C_2H_2$, $C_2H_4$, and $CH_4$.

Preferably, the performing the pre-learning for the unlabeled data and the pseudo label data among the scaled dissolved gas analysis data includes defining a loss function $$L_{DNN}(\theta) = \alpha L_{su}\left(\tilde{Y}_s, \hat{Y}_{end}\right) + (1 - \alpha)L_{un}\left(X_s^*, \hat{X}_{end}^*\right)$$

of a deep neural network, selecting a hyper parameter $\alpha$ for adjusting a first term $L_{su}$ and a second term, $L_{un}$ in in right terms of the loss function, and acquiring an optimal parameter by using a backpropagation method so as to optimize the loss function.

Preferably, in the loss function, $L_{su}$ represents a difference between pseudo label data $\tilde{Y}_s$ acquired through a Duval's triangle method and pseudo label data $\hat{Y}_{end}$ estimated in a last layer among hidden layers of the deep neural network.

Preferably, in the loss function, $L_{un}$ represents a difference between unlabeled data $$X_s^*$$

among the scaled dissolved gas analysis data and dissolved gas analysis data $$\hat{X}_{end}^*$$

estimated in the last layer among the hidden layers of the deep neural network.

Preferably, the performing of the re-learning for the labeled data through transfer of the parameter optimized by performing the pre-learning includes preparing for learning of the labeled data, freezing some hidden layers of the deep neural network, performing learning only for the last hidden layer other than the freezing hidden layers, and acquiring the optimal parameter by using the backpropagation method so as to optimize the loss function.

Preferably, in the freezing of some hidden layers of the deep neural network, the remaining hidden layers other than the last hidden layer are frozen.

Advantageous Effects

According to an embodiment of the present invention, an advantage of a rule-based learning method that diagnoses a malfunction state of the data without labeled data and an advantage of a deep learning based learning method based on artificial intelligence are fused to accurately perform malfunction diagnosis of a transformer even in a situation in which there are multiple dissolved gas analysis data, but only a minority of labeled data.

Further, since it is possible to fuse the knowledge of an expert through the rule-based learning method without relying only on the deep learning based learning method based on the artificial intelligence when diagnosing the malfunction of the transformer, the accuracy of the deep learning based learning method can be improved without developing a difficult and complex model.

DESCRIPTION OF DRAWINGS

FIG. 1 is a diagram illustrating a malfunction diagnosis method using a Duval's triangle method.

FIG. 2 is a diagram illustrating a transformer malfunction diagnosis device according to an embodiment of the present invention.

FIG. 6 is a diagram illustrating a comparison of diagnosis accuracies of a transformer malfunction diagnosis method in the related art and diagnosis accuracy of a transformer malfunction diagnosis method according to an embodiment of the present invention.

BEST MODE

Figure 3:
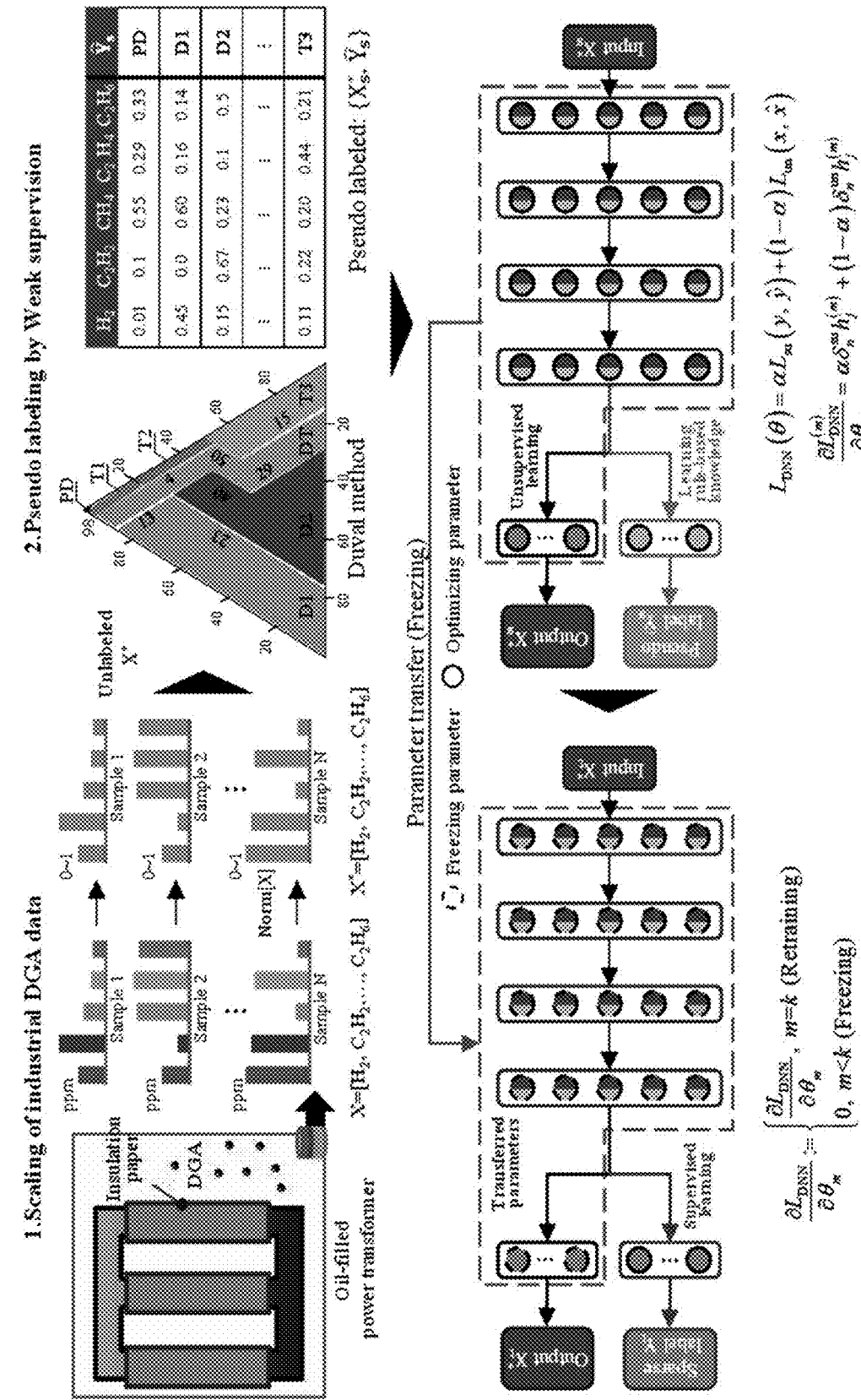
FIG. 3 is a diagram totally illustrating a transformer malfunction diagnosis method according to an embodiment of the present invention.

Hereinafter, a preferred embodiment of the present invention will be described in detail with reference to the accompanying drawings. First, when reference numerals refer to components of each drawing, it is to be noted that although the same components are illustrated in different drawings, the same components are denoted by the same reference numerals as possible. Further, in describing the present invention, a detailed description of known related configurations and functions may be omitted to avoid unnecessarily obscuring the subject matter of the present invention. Further, hereinafter, the preferred embodiment of the present invention will be described, but the technical spirit of the present invention is not limited thereto or restricted thereby and the embodiments can be modified and variously executed by those skilled in the art.

FIG. 1 is a diagram illustrating a malfunction diagnosis method using a Duval's triangle method.

A transformer malfunction diagnosis method, which diagnoses a malfunction type (e.g., heat, electricity, and partial discharging) of the oil immersed transformer using dissolved gas analysis (DGA) data may be generally divided into two methods, i.e., a rule-based learning method and an AI-based learning method.

First, the rule-based learning as a method for driving a result value for a given input means a method for learning and predicting according to a firm rule. Further, the rule-based learning may be made based on a handcrafted feature made through physical knowledge and experience of an expert by utilizing the dissolved gas analysis (DGA) data.

Referring to FIG. 1, in a Duval's triangle method which is one of the rule-based learning methods, a gas composition ratio may be derived from concentrations of $C_2H_2$, $C_2H_4$, and $CH_4$ which are three combustible gases.

In this case, respective gas composition ratios derived from the concentrations of $C_2H_2$, $C_2H_4$, and $CH_4$ which are three combustible gases may be expressed as in Equation 1 below.

$$R_i = \text{Gas}_i \bigg/ \sum_{i=1}^{3} \text{Gas}_i \text{ where Gas}_i \in \{C_2H_2, C_2H_4, CH_4\} \qquad \text{[Equation 1]}$$

In the Duval's triangle method, a malfunction identification of the transformer may be exemplarily represented as seven types, i.e., partial discharge (PD), discharge of low energy arcing (D1), discharge of low-energy arcing (D2), thermal malfunction of low-level arcing (T1, in the case of a temperature less than 300° C.), thermal malfunction of medium-level arcing (T2, in the case of a temperature more than 300° C. and less than 700° C.), thermal malfunction of high-level arcing (T3, in the case of a temperature more than 700° C.), and thermal and discharge malfunctions (DT) by using the gas composition ratios (e.g., R1, R2, and R3) derived through Equation 1 above.

A malfunction diagnosis result based on the malfunction identification may be intuitively described on a coordinate plane of a Duval's triangle in terms of the gas composition ratios R1, R2, and R3 derived through Equation 1 above as illustrated in FIG. 1.

However, such a Duval's triangle method may adopt features based on human experience, and may have a lower malfunction diagnosis capability than an AI-based learning based on sufficient mathematical formulation and statistical approach.

Specifically, in the case of the Duval's triangle method as illustrated in FIG. 1, there is no requirement for training data or optimization process, so a lot of calculation work is not required, and there is an advantage in that an error state of unlabeled dissolved gas analysis data may be easily identified. However, in the case of the Duval's triangle method, multiple mathematical formulations are lacked, and the Duval's triangle method is based on a human experiential method in all models, so accuracy may be relatively lower than the AI-based learning method and an incomplete diagnosis result may be shown.

Meanwhile, the AI-based learning method includes a deep-learning based learning method, and in the malfunction diagnosis method of the transformer of the deep-learning based learning method, a deep neural network (DNN) may be exemplarily used.

The deep neural network (DNN) may mean a neural network with a hidden layer in which several layers constituted by a plurality of nodes, and activation function that associates an input response and an output response in the node are stacked. Preferably, the deeper the depth of the hidden layers in the deep neural network (DNN), the input response and the output response may extract higher dimensional features.

In the deep neural network (DNN), a sample of the training data may be expressed as $\{(x^{(1)}, y^{(1)}), \ldots, (x^{(p)}, y^{(p)})\}$. In this case, p may represent the number of samples of the dissolved gas analysis data, $x^{(m)}$ may represent input dissolved gas analysis data (input response), and $y^{(m)}$ may represent information (output response) one-hot encoded so as to be learned by the deep neural network (DNN). In this case, the one-hot encoding method means converting a text into a significant number (or vector) for deep learning in the deep-learning based learning method.

An activation function f may be a SoftMax function, and linearize the $x^{(m)}$ into $z^{(m)}$ which is activated dissolved gas analysis data by using a parameter $\theta$ (exemplarily including w and b as in Equation 2 below) as in Equation 2 below, and convert the linearized $z^{(m)}$ into $h^{(m)}$ which is a hidden unit.

$$h^{(m)} = f(z^{(m)}) = f(Wx^{(m)} + b) \qquad \text{[Equation 2]}$$

In Equation 2, W may represent a weight which represents a directionality or form of a linear boundary, and b may mean a bias vector which represents a fragment of the linear boundary.

Meanwhile, in the deep neural network (DNN), $x^{(m)}$ and $y^{(m)}$ may be associated with each other as in Equation 3 below.

$$\hat{y}_{end}^{(m)} = q_{sm}\left(W_N f_{N-1}\left(\ldots f_{N-1}\left(W_1 x^{(m)} + b_1\right) \ldots \right) + b_N\right) \qquad \text{[Equation 3]}$$

In Equation 3, $q_{sm}$ may mean a SoftMax function placed in a last layer among the hidden layers of the deep neural network (DNN), and in Equation 2 above, $h^{(m)}$ may be converted into a one-hot encoded vector $\hat{y}^{(m)}$ including probability information of $y^{(m)}$. In this case, in Equation 3, $$\hat{y}_{end}^{(m)}$$

may mean an encoded vector value in the last hidden layer when the deep neural network (DNN) has N hidden layers.

Meanwhile, in Equation 3, $q_{sm}$ may be expressed as in Equation 4 below.

$$q_{sm}(z_n^{(m)}) = \exp(z_n^{(m)}) \bigg/ \sum_{n=1}^{C} \exp(z_n^{(m)}) \qquad \text{[Equation 4]}$$

The parameter $\theta$ needs to be optimized by minimizing a loss function in order to associate

7

$$\hat{y}_{end}^{(m)} \text{ and } \hat{y}^{(m)},$$

and the loss function may be expressed as in Equation 5 below.

$$L(y, \hat{y}_{end}) = -\frac{1}{p}\sum_{m=1}^{p} y^{(m)}\log(\hat{y}_{end}^{(m)}) \quad \text{[Equation 5]}$$

In Equation 5, the loss function L may mean a difference between y and $\hat{y}_{end}$.

Further, in order to optimize Equation 5, optimal parameters may be acquired by using a backpropagation method as in Equation 6 below. Preferably, the backpropagation method may be performed by a mini-batch gradient descent (MGD) algorithm.

$$\theta_{nj}^{N} \leftarrow \theta_{nj}^{N} - \eta \frac{\partial L^{(m)}}{\partial \theta_{nj}^{N}} \left( \frac{\partial L^{(m)}}{\partial \theta_{nj}^{N}} = \delta_{n}^{L} \frac{\partial z_{n}^{(m)}}{\partial \theta_{nj}^{N}} = \delta_{n}^{L} h_{j}^{(m)} \right) \quad \text{[Equation 6]}$$

In Equation 6 above, $\theta^{N}$ may mean an optimized parameter, and $\eta$ may mean a learning rate. Further, $\theta^{N}$ may mean a parameter in the last hidden layer among the hidden layers of the deep neural network (DNN).

Through such a process, the input dissolved gas analysis data and output information may be associated with each other in the deep neural network (DNN).

However, the deep learning scheme including the deep neural network (DNN) operates well under a general assumption that the training data and test data are extracted in the same distribution, but there is a problem in that in an actual transformer malfunction diagnosis environment, the amount of malfunction data or labeled data is very insufficient due to huge maintenance cost in terms of data collection, so the deep learning scheme does not operate well.

In order to solve such a problem, transfer learning may be used, and the transfer learning may also be applied in a situation in which given data is not sufficient, so the transfer learning has been spotlighted in a malfunction diagnosis related field of the transformer in recent years.

Preferably, the transfer learning may mean transmitting information (e.g., the optimized parameter) acquired from unlabeled data which is source data to labeled data which is target data. In this case, a training model in the unlabeled data may be defined as a pre-trained model and a training model in the labeled data may be defined as a re-trained model.

Further, the transfer learning may significantly enhance malfunction diagnosis performance in a target domain including the labeled data by reusing the pre-trained model, and freezing, partial freezing, fine-tuning, and selective parameter freezing are provided according to a size of the labeled data, and preferably, when the amount of the unlabeled data is much larger than the labeled data, the freezing scheme may be primarily used.

Here, performing malfunction diagnosis of the transformer by combining the rule-based learning method and the AI-based learning method will be described in detail.

FIG. 2 is a diagram illustrating a malfunction diagnosis device 100 of a transformer according to an embodiment of the present invention and FIG. 3 is a diagram totally illustrating a transformer malfunction diagnosis method according to an embodiment of the present invention.

Referring to FIG. 2 the malfunction diagnosis device 100 includes a data scaling unit 10, a pseudo label data acquisition unit 20, a pre-learning unit 30, and a re-learning unit 40.

In the embodiment, the data scaling unit 10 and the pseudo label data acquisition unit 20 may perform the malfunction diagnosis of the transformer according to the rule-based learning method, and the pre-learning unit 30 and the re-learning unit 40 may perform the malfunction diagnosis of the transformer according to the AI-based learning method.

Referring to FIGS. 2 and 3, the data scaling unit 10 may scale the dissolved gas analysis data acquired from the transformer. Preferably, the dissolved gas analysis data includes the unlabeled data and the labeled data, and in FIG. 3, the dissolved gas analysis data acquired from the transformer may be written as X and the scaled (scale-converted) dissolved gas analysis data may be written as X*.

Preferably, the data scaling unit 10 may be constituted by a data logization unit 12 and a data regularization unit 14.

First, the data logization unit 12 may logizate the dissolved gas analysis data as illustrated in FIG. 3. In general, a physical unit of the dissolved gas analysis data may be ppm, and the dissolved gas analysis data is logizated through the data logization unit 12 in order to minimize overshooting of a value of the dissolved gas analysis data when the malfunction of the transformer occurs.

Next, the data regularization unit 14 may regularize the logizated dissolved gas analysis data (exemplarily regularize within a range of [0, 1].

As a result, the optimization of the parameter may be stably made upon the AI-based learning made by the pre-learning unit 30 and the re-learning unit 40, and computation may be rapidly made by the AI-based learning.

The logization and regularization processes of the dissolved gas analysis data through the data scaling unit 10 may be exemplarily expressed as in Equation 7 below. Equation 7 below exemplarily illustrates a process of logizating and regularizing the unlabeled data among the dissolved gas analysis data.

$$X \rightarrow \log(X) \rightarrow MinMax(\log(X)) \rightarrow X_s^* \quad \text{[Equation 7]}$$

Figure 4:
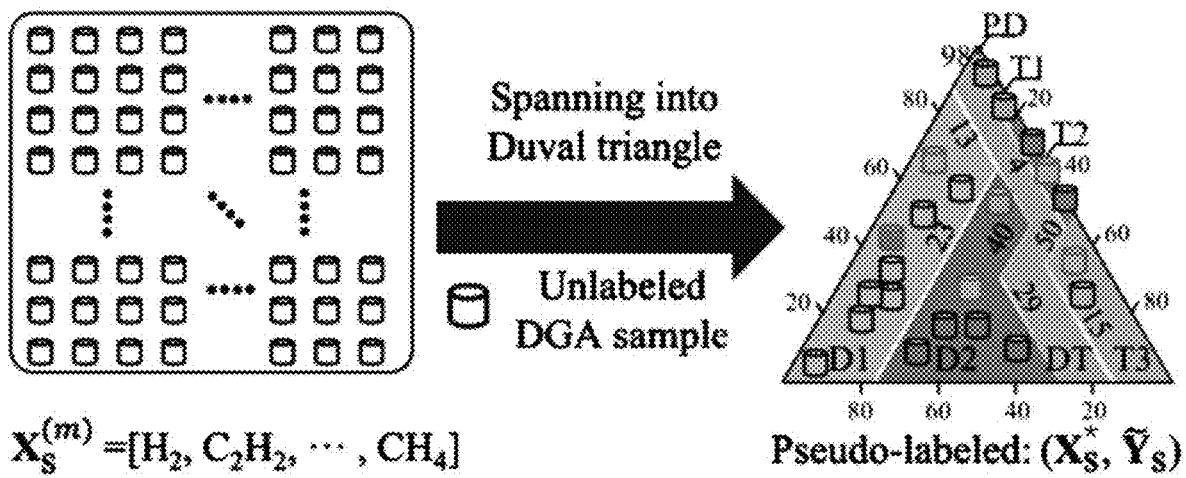
FIG. 4 is a diagram illustrating a process of converting scaled dissolved gas analysis data into pseudo label data by using a Duval's triangle method.

FIG. 4 is a diagram illustrating a process of converting scaled dissolved gas analysis data X* into pseudo label data by using a Duval triangle method. Preferably, the process of converting the unlabeled data among the scaled dissolved gas analysis data into the pseudo label data may be made through shallow supervised learning of a Duval's triangle method.

Referring to FIGS. 2 to 4, the pseudo label data acquisition unit 20 may convert the unlabeled data among the scaled dissolved gas analysis data into the pseudo label data and acquire the pseudo label data by using the Duval's triangle method.

Preferably, the pseudo label data acquisition unit 20 may be constituted by a transformer state classification unit 22, a gas composition ratio derivation unit 24, a pseudo label data acquisition unit 26, and a pre-learning preparation unit 28.

First, the transformer state classification unit 22 may classify a normal state and a malfunction state of the transformer by using the unlabeled data among the scaled dissolved gas analysis data according to the rule-based learning method.

In this case, the normal state and the malfunction state of the transformer may be classified based on a normal threshold of each combustible gas shown in Table 1 below.

TABLE 1

| | Gas | | | | |
|---|---|---|---|---|---|
| | $H_2$ | $C_2H_2$ | $C_2H_4$ | $C_2H_6$ | $CH_4$ |
| Normal threshold (ppm) | 60~150 | 3~50 | 60~280 | 50~90 | 40~110 |

Next, the gas composition ratio derivation unit 24 selects three combustible gases $C_2H_2$, $C_2H_4$, and $CH_4$ to derive the gas composition ratios from concentrations of $C_2H_2$, $C_2H_4$, and $CH_4$ as in Equation 1 described above.

Next, the pseudo label data acquisition unit 26 applies sample data of the derived gas composition ratios to the Duval's triangle method as illustrated in FIGS. 1 and 3 to convert the unlabeled data among the scaled dissolved gas analysis data into the pseudo label data. The pseudo label data converted through the Duval's triangle method may be exemplarily acquired as in [1,0,0,0,0].

Last, the pre-learning preparation unit 28 may prepare for $$X_s^* \text{ and } \check{Y}_s$$

to be used as the training data to be trained by the pre-learning unit 30 described above as illustrated in FIGS. 3 and 4. In this case, the $$X_s^* \text{ and } \check{Y}_s$$

may mean the unlabeled data and pseudo label data corresponding thereto, respectively among the scaled dissolved gas analysis data.

Referring to FIGS. 2 and 3, the pre-learning unit 30 may pre-learn the deep neural network (DNN) through an auxiliary unsupervised-based regularization process. In this case, a learning process made through the pre-learning unit 30 may be regarded as updating the parameter so as to minimize a loss function $L_{su}$ in supervised learning.

Preferably, the pre-learning unit 30 may be constituted by a loss function definition unit 32, a hyper parameter selection unit 34, and a first optimal parameter acquisition unit 36.

First, the loss function definition unit 32 may convert and define the loss function shown in Equation 5 described above as in Equation 8 below. In this case, $L_{DNN}(\theta)$ may be a loss function considered in the process of training the deep neural network (DNN), and may be defined as in Equation 8 below.

$$L_{DNN}(\theta) = \alpha L_{su}\left(\check{Y}_s, \hat{Y}_{end}\right) + (1 - \alpha)L_{un}\left(X_s^*, \hat{X}_{end}^*\right) \quad \text{[Equation 8]}$$

In this case, in Equation 8 above, $L_{su}$ may be a loss function that represents a difference between the pseudo label data $\check{Y}_s$ acquired through the Duval's triangle method in the supervised learning through the pseudo label data acquisition unit 20 and estimated pseudo label data $\hat{Y}_{end}$ in the last layer among the hidden layers of the deep neural network (DNN).

Further, $L_{un}$ may be a loss function that represents a difference between the unlabeled data $$X_s^*$$

among the scaled dissolved gas analysis data in the unsupervised learning and the estimated dissolved gas analysis data $$\hat{X}_{end}^*$$

in the last layer among the hidden layers of the deep neural network (DNN). Preferably, may be performed as a regularization process for minimizing an overfitting problem of the supervised learning.

Further, $\alpha$ may mean a hyper parameter which is a weight between $L_{su}$ and $L_{un}$, and preferably, may be configured by values between 0 and 1.

A first term among right terms of Equation 8 above may be included as a purpose of the supervised learning similarly to the loss function in Equation 5, but a second term may mean re-learning an input value X (the unlabeled data among the dissolved gas analysis data). As a result, even when using the pseudo label data $\check{Y}_s$ wrongly acquired by the pseudo label data acquisition unit 20, the pre-learning unit 30 may complement the wrongly acquired pseudo label data through re-learning of the input value X (the unlabeled data among the dissolved gas analysis data).

Next, the hyper parameter selection unit 34 may select a hyper parameter $\alpha$ for adjusting the first term $L_{su}$ and the second term $L_{un}$ among the right terms of Equation 8 above.

Last, the first optimal parameter acquisition unit 36 may acquire optimal parameters by using the backpropagation method as in Equation 9 below in order to optimize Equation 8 above.

$$\theta_{nj} \leftarrow \theta_{nj} - \eta \frac{\partial L_{DNN}^{(m)}}{\partial \theta_{nj}}, \left(\frac{\partial L_{DNN}^{(m)}}{\partial \theta_{nj}} = \alpha \delta_n^{su} h_j^{(m)} + (1 - \alpha)\delta_n^{un} h_j^{(m)}\right) \quad \text{[Equation 9]}$$

In Equation 9, each of $$\delta_n^{su}$$

and $$\delta_n^{un}$$

may be expressed as in Equation 10 below.

$$\delta_n^{su} \equiv \frac{\partial L_{su}^{(m)}}{\partial z_n^{(m)}} = f_{su}'\left(z_n^{(m)}\right) \frac{\partial L_{su}^{(m)}}{\partial \hat{Y}_{end}^{(m)}}, \quad \text{[Equation 10]}$$

$$\delta_n^{un} \equiv \frac{\partial L_{un}^{(m)}}{\partial z_n^{(m)}} = f_{un}'\left(z_n^{(m)}\right) \frac{\partial L_{un}^{(m)}}{\partial \hat{X}_{end}^{*(m)}}$$

Referring to FIGS. 2 and 3, the re-learning unit 40 may perform re-learning the data pre-learned by the pre-learning unit 30 through parameter transfer of the deep neural network (DNN).

Preferably, the re-learning unit 40 may be constituted by a re-learning preparation unit 41, a hidden layer freezing unit 42, a hidden layer learning unit 43, a second optimal parameter acquisition unit 44, and a verification unit 45.

First, the re-learning preparation unit 41 may prepare for learning of labeled data $$X_t^* \text{ and } Y_t.$$

Preferably, the $$X_t^* \text{ and } Y_t$$

may mean the labeled data among the scaled dissolved gas analysis data and a value indicating an actual malfunction state corresponding thereto, respectively.

Next, the hidden layer freezing unit 42 may freeze some hidden layers of the deep neural network (DNN).

As described above, the transfer learning may adopt the freezing scheme when the amount of the unlabeled data is much larger than that of the labeled data.

The hidden layer freezing unit 42 may perform the transfer learning according to the freezing scheme by assuming that the amount of the labeled data is much larger than the amount of the unlabeled data. In this case, parameters in all remaining hidden layers other than the last hidden layer may be frozen through the hidden layer freezing unit 42.

In this case, the parameter frozen by the hidden layer freezing unit 42 may be a parameter optimized through the unsupervised learning among the parameters optimized through the pre-learning unit 30.

The hidden layer freezing unit 42 may freeze the remaining hidden layers other than the last hidden layer as in Equation 11 below, and a parameter for a last hidden layer which is not frozen may be a parameter optimized through the supervised learning among the parameters optimized through the pre-learning unit 30.

$$\frac{\partial L_{DNN}}{\partial \theta^m} = \begin{cases} \frac{\partial L_{DNN}}{\partial \theta^m}, & m = N \ \& \ \text{Supervised task (Re-training)} \\ 0, & \text{otherwise (Freezing)} \end{cases} \quad \text{[Equation 11]}$$

In Equation 11 above, m represents an N-th hidden layer and N means the total number of hidden layers.

Next, the hidden layer learning unit 43 may perform learning according to Equation 8 described above, and does not learn the frozen hidden layer, but perform learning (re-learning) only for the last hidden layer.

Next, the second optimal parameter acquisition unit 44 optimizes the parameters in the supervised learning by using Equations 8 to 10 described above again to acquire the optimal parameter. In this case, the loss function in Equations 8 described above may be constituted by $$X_t^* \text{ and } Y_t.$$

Last, the verification unit 45 tests the training model derived through the above-described method with the labeled data $$X_t^* \text{ and } Y_t$$

to verify the accuracy.

Figure 5:
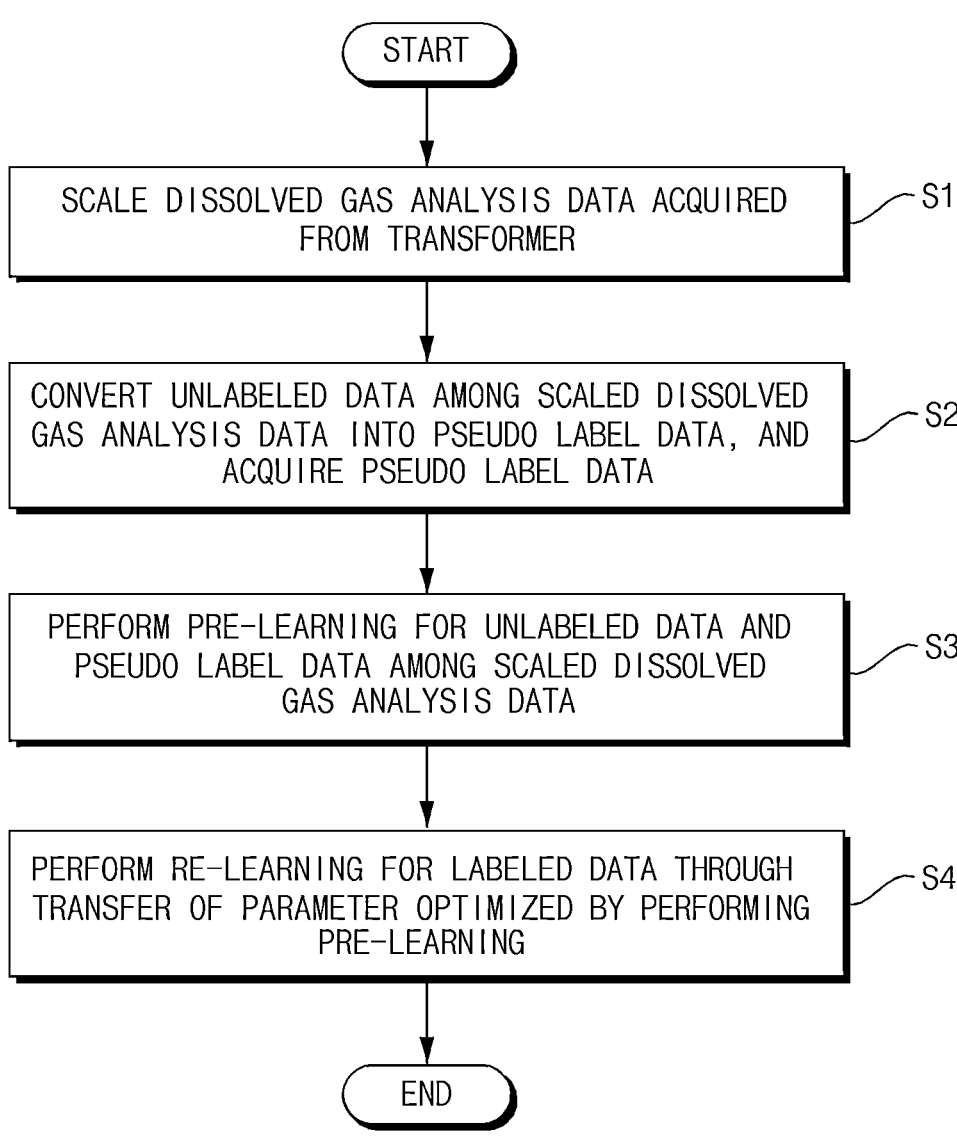
FIG. 5 is a flowchart illustrating a transformer malfunction diagnosis method according to an embodiment of the present invention.

FIG. 5 is a flowchart illustrating a transformer malfunction diagnosis method according to an embodiment of the present invention.

Referring to FIG. 5, the malfunction diagnosis method of the transformer according to an embodiment of the present invention is as follows.

First, the dissolved gas analysis data acquired from the transformer is scaled (step S1).

Step S1 above may include a step of logizating the dissolved gas analysis data and a step of regularizing the logizated dissolved gas analysis data, and step S1 may be performed by the data scaling unit 10.

Next, unlabeled data $$X_s^*$$

among the scaled dissolved gas analysis data X* in step S1 above is converted into pseudo label data $\tilde{Y}_s$, and acquired (step S2).

Step S2 above may include a step of classifying a normal state and a malfunction state of the transformer by using unlabeled data among the scaled dissolved gas analysis data, a step of selecting three combustible gases and deriving gas composition ratios from concentrations of respective combustible gases, a step of converting the unlabeled data into the pseudo label data among the scaled dissolved gas analysis data by applying the derived gas composition ratios to a Duval's triangle method, and a step of preparing for the unlabeled data $$X_s^*$$

and the pseudo label data $\tilde{Y}_s$ among the scaled dissolved gas analysis data, and step S2 may be performed by the pseudo label data acquisition unit 20. Preferably, three combustible gases selected by the pseudo label data acquisition unit 20 may be $C_2H_2$, $C_2H_4$, and $CH_4$.

Next, pre-learning for the unlabeled data and the pseudo label data among the scaled dissolved gas analysis data is performed (step S3).

Step S3 may include a step of defining a loss function $$L_{DNN}(\theta) = \alpha L_{su}\left(\hat{Y}_s, \hat{Y}_{end}\right) + (1-\alpha) L_{un}\left(X_s^*, \hat{X}_{end}^*\right)$$

of a deep neural network (DNN), a step of selecting a hyper parameter $\alpha$ for adjusting a first term $L_{su}$ and a second term $L_{un}$ in right terms of the loss function, and a step of acquiring an optimal parameter by using a backpropagation method so as to optimize the loss function, and step S3 may be performed by the pre-learning unit 30.

Preferably, the step of performing the pre-learning may be performed at multiple times (e.g., 200 times).

Last, re-learning the labeled data is performed through transfer of the parameter optimized by performing the pre-learning (step S4).

Step S4 above may include a step of preparing for learning of the labeled data $$X_t^* \text{ and } Y_t,$$

a step of freezing some hidden layers of the deep neural network (DNN), a step of performing learning only for the last hidden layer other than the frozen hidden layer, and a step of acquiring the optimal parameter by using the back-propagation method so as to optimize the loss function, and step S4 may performed by the re-learning unit 40.

In this case, in the step of freezing some hidden layers of the deep neural network (DNN), all remaining hidden layers other than the last hidden layer may be frozen, and the step of performing the re-learning may be performed at multiple times (e.g., 20 times).

FIG. 6 is a diagram illustrating a comparison of diagnosis accuracies of a transformer malfunction diagnosis method in the related art and diagnosis accuracy of a transformer malfunction diagnosis method according to an embodiment of the present invention.

Referring to FIG. 6, a result represented by summarizing an accuracy result of transformer malfunction diagnosis by comparing the malfunction diagnosis method of the transformer according to the embodiment of the present invention with the malfunction diagnosis method of the transformer in the related art with respect to the amount of the labeled training data may be confirmed through a table.

In this case, in FIG. 6, a first learning approach indicates a case of supervised learning which learning is performed only with the labeled data, a second learning approach indicates a case of semi-supervised learning in which both the labeled data and unlabeled data are learned, and a third learning approach indicates a malfunction diagnosis method (rule-based knowledge learning) of the transformer using a rule-based method and an AI-based method.

Further, in FIG. 6, L-SVM means a linear support vector machine, R-SVM means a support vector machine having a radial basis function, KNN means a K-nearest neighbors algorithm, 1-NN means a neural network having one hidden layer, and DeA means a deep autoencoder. The L-SVM, R-SVM, KNN, 1-NN, and DeA are representative AI-based analysis methods, so a detailed description thereof is omitted.

Meanwhile, in the third learning approach of FIG. 6, the diagnosis method using the deep neural network (DNN) may be represented as $$DNN_{FT}^{Non}, DNN_{PF}^{Non}, DNN_{FT}^{Aux},$$

and BDD. In this case, "Non" means that auxiliary unsupervised learning through pre-learning unit 30 is not made, and "Aux" means that the auxiliary unsupervised learning through the pre-learning unit 30 is made. Further, "PF" means that parameter freezing is made through the re-learning unit 40, "FT" means that fine tuning is made, and "BDD" means the malfunction diagnosis method of the transformer according to the embodiment, which bridges a Duval's triangle method and a deep neural network method.

Referring to FIG. 6, it may be confirmed that in all diagnosis methods, as the amount of the labeled training data increases, the malfunction diagnosis accuracy of the transformer increases.

In this case, it may be confirmed that the malfunction diagnosis method of the transformer (BDD) according to the embodiment, which bridges the rule-based method and the deep learning based method achieves the highest malfunction diagnosis accuracy as compared with other diagnosis methods regardless of the amount of the labeled training data.

In particular, it may be confirmed that in the case of the malfunction diagnosis method of the transformer according to the embodiment of the present invention, the highest malfunction diagnosis performance is achieved even under a condition in which there is rare labeled data exists.

Exemplarily, it may be confirmed that in the case of the malfunction diagnosis method of the transformer according to the embodiment of the present invention, the highest malfunction diagnosis accuracy (86.4%) is achieved compared with other diagnosis methods even when only 5% of labeled training data exists.

Further, it may be confirmed that in the case of the malfunction diagnosis method of the transformer according to the embodiment of the present invention, the highest malfunction diagnosis accuracy (95.4%) is most quickly achieved compared with other diagnosis methods even when only 30% of labeled training data exists.

According to an embodiment of the present invention, an advantage of a rule-based learning method that diagnoses a malfunction state without labeled data and an advantage of a deep learning based learning method based on artificial intelligence are fused to accurately perform malfunction diagnosis of a transformer even in a situation in which there are multiple dissolved gas analysis data, but only a minority of labeled data.

Further, since it is possible to fuse the knowledge of an expert through the rule-based learning method without relying only on the deep learning based learning method based on the artificial intelligence when diagnosing the malfunction of the transformer, the accuracy of the deep learning based learning method can be improved without developing a difficult and complex model.

The above description just illustrates the technical spirit of the present invention and various changes, modifications, and substitutions can be made by those skilled in the art to which the present invention pertains without departing from an essential characteristic of the present invention. Therefore, the embodiments and the accompanying drawings disclosed in the present invention are used to not limit but describe the technical spirit of the present invention and the scope of the technical spirit of the present invention is not limited by the embodiments and the accompanying drawings. The protection scope of the present invention should be construed based on the following appended claims and it should be appreciated that the technical spirit included within the scope equivalent to the claims belongs to the scope of the present invention.

The invention claimed is:

1. A transformer malfunction diagnosis device, comprising:

a data scaling unit scaling dissolved gas analysis data acquired from the transformer;

a pseudo label data acquisition unit converting unlabeled data among the scaled dissolved gas analysis data into pseudo label data, and acquiring the pseudo label data by applying derived gas composition ratios from combustible gases to a Duval's triangle method;

a pre-learning unit performing pre-learning for the unlabeled data and the pseudo label data among the scaled dissolved gas analysis data; and a re-learning unit performing re-learning for labeled data through transfer of a parameter acquired by optimizing a loss function using a backpropagation method during the pre-learning, wherein the re-learning unit freezes one or more hidden layers of a deep neural network during the re-learning.

2. The transformer malfunction diagnosis device of claim 1, wherein the data scaling unit includes a data logger logging the dissolved gas analysis data, and a data regularization unit regularizing the logged dissolved gas analysis data.

3. The transformer malfunction diagnosis device of claim 1, wherein the pseudo label data acquisition unit includes a transformer state classification unit classifying a normal state and a malfunction state of the transformer by using the unlabeled data among the scaled dissolved gas analysis data, a gas composition ratio derivation unit selecting three combustible gases, and deriving the gas composition ratios from concentrations of respective combustible gases, a pre-learning preparation unit preparing for the unlabeled data and the pseudo label data among the scaled dissolved gas analysis data.

4. The transformer malfunction diagnosis device of claim 3, wherein the three combustible gases are $C_2H_2$, $C_2H_4$, and $CH_4$.

5. The transformer malfunction diagnosis device of claim 1, wherein the pre-learning unit includes a loss function definition unit defining the loss function $$L_{DNN}(\theta) = \alpha L_{su}(\hat{Y}_s, \hat{Y}_{end}) + (1-\alpha)L_{un}(X_s^*, \hat{X}_{end}^*)$$

of a deep neural network, and a hyper parameter selection unit selecting a hyper parameter $\alpha$ for adjusting a first term $L_{su}$ and a second term $L_{un}$ in right terms of the loss function.

6. The transformer malfunction diagnosis device of claim 5, wherein in the loss function, $L_{su}$ represents a difference between pseudo label data $\tilde{Y}_s$ acquired through a Duval's triangle method and pseudo label data $\hat{Y}_{end}$ estimated in a last layer among hidden layers of the deep neural network.

7. The transformer malfunction diagnosis device of claim 5, wherein in the loss function, $L_{un}$ represents a difference between unlabeled data $$X_s^*$$

among the scaled dissolved gas analysis data and dissolved gas analysis data $$\hat{X}_{end}^*$$

estimated in the last layer among the hidden layers of the deep neural network.

8. The transformer malfunction diagnosis device of claim 5, wherein the re-learning unit includes a re-learning preparation unit preparing for learning of the labeled data, a hidden layer freezing unit freezing the one or more hidden layers of the deep neural network, and a hidden layer learning unit performing learning only for the last hidden layer other than the frozen hidden layers.

9. The transformer malfunction diagnosis device of claim 8, wherein the hidden layer freezing unit freezes the remaining hidden layers other than the last hidden layer.

10. A transformer malfunction diagnosis method, comprising:

scaling dissolved gas analysis data acquired from the transformer;

converting unlabeled data among the scaled dissolved gas analysis data into pseudo label data by applying derived gas composition ratios from combustible gases to a Duval's triangle method, and acquiring the pseudo label data;

performing pre-learning for the unlabeled data and the pseudo label data among the scaled dissolved gas analysis data; and performing re-learning for labeled data through transfer of a parameter acquired by optimizing a loss function using a backpropagation method during the pre-learning, wherein the performing of the re-learning comprises freezing one or more hidden layers of a deep neural network.

11. The transformer malfunction diagnosis method of claim 10, wherein the scaling of the dissolved gas analysis data includes logging the dissolved gas analysis data, and regularizing the logged dissolved gas analysis data.

12. The transformer malfunction diagnosis method of claim 10, wherein the converting of the unlabeled data among the scaled dissolved gas analysis data into pseudo label data, and acquiring of the pseudo label data includes classifying a normal state and a malfunction state of the transformer by using the unlabeled data among the scaled dissolved gas analysis data, selecting three combustible gases, and deriving the gas composition ratios from concentrations of respective combustible gases, and preparing for the unlabeled data and the pseudo label data among the scaled dissolved gas analysis data.

13. The transformer malfunction diagnosis method of claim 12, and wherein the three combustible gases are $C_2H_2$, $C_2H_4$, and $CH_4$.

14. The transformer malfunction diagnosis method of claim 10, wherein performing the pre-learning for the unlabeled data and the pseudo label data among the scaled dissolved gas analysis data includes defining the loss function $$L_{DNN}(\theta) = \alpha L_{su}(\hat{Y}_s, \hat{Y}_{end}) + (1-\alpha)L_{un}(X_s^*, \hat{X}_{end}^*)$$

of a deep neural network, and selecting a hyper parameter $\alpha$ for adjusting a first term $L_{su}$ and a second term $L_{un}$ in right terms of the loss function.

15. The transformer malfunction diagnosis method of claim 14, wherein in the loss function, $L_{su}$ represents a difference between pseudo label data $\tilde{Y}_s$ acquired through a Duval's triangle method and pseudo label data $\hat{Y}_{end}$ estimated in a last layer among hidden layers of the deep neural network.

16. The transformer malfunction diagnosis method of claim 14, wherein in the loss function, $L_{un}$ represents a difference between unlabeled data $$X_s^*$$

among the scaled dissolved gas analysis data and dissolved gas analysis data $$\hat{X}_{end}^*$$

estimated in the last layer among the hidden layers of the deep neural network.

17. The transformer malfunction diagnosis method of claim 14, wherein the performing of the re-learning for the labeled data through transfer of the parameter optimized by performing the pre-learning includes preparing for learning of the labeled data, and performing learning only for the last hidden layer other than the frozen hidden layers.

18. The transformer malfunction diagnosis method of claim 17, wherein in the freezing of the one or more hidden layers of the deep neural network, the remaining hidden layers other than the last hidden layer are frozen.

\* \* \* \* \*